United States Patent
Jacobsen et al.

[11] 3,935,274
[45] Jan. 27, 1976

[54] PROCESS FOR THE CONTINUOUS PREPARATION OF HYDROXYPIVALDEHYDE

[75] Inventors: Günter Jacobsen, Frankfurt am Main; Hans Fernholz, Fischbach, Taunus; Dieter Freudenberger, Hofheim, Taunus, all of Germany

[73] Assignee: Hoechst Aktiengesellschaft, Frankfurt am Main, Germany

[22] Filed: Apr. 21, 1969

[21] Appl. No.: 817,961

[30] Foreign Application Priority Data
Apr. 24, 1968 Germany.......................... 1768274

[52] U.S. Cl.......... 260/602; 260/484 R; 260/530 R; 260/635 A; 260/635 P
[51] Int. Cl............................................. C07c 47/18
[58] Field of Search ....................... 260/602, 635 P

[56] References Cited
UNITED STATES PATENTS

| | | | |
|---|---|---|---|
| 2,442,280 | 5/1948 | Alheritiere.......................... | 260/602 |
| 2,517,013 | 8/1950 | Miller et al......................... | 260/602 |
| 2,763,693 | 9/1956 | Vander Woude et al. ... | 260/604 HF |
| 2,811,562 | 10/1957 | Hagemeyer.......................... | 260/602 |
| 2,863,878 | 12/1958 | Lynn.................................. | 260/602 |

FOREIGN PATENTS OR APPLICATIONS

| | | | |
|---|---|---|---|
| 140,089 | 7/1947 | Australia............................ | 260/602 |
| 834,100 | 5/1960 | United Kingdom................ | 260/602 |
| 958,654 | 5/1964 | United Kingdom............ | 260/635 P |
| 634,562 | 3/1950 | United Kingdom................ | 260/602 |

OTHER PUBLICATIONS
Hagemeyer et al., The Chem. of Isobutyraldehyde, p. 5, 1953.

*Primary Examiner*—Joseph E. Evans
*Attorney, Agent, or Firm*—Curtis, Morris & Safford

[57] ABSTRACT

Process for the continuous preparation of hydroxypivalaldehyde by the reaction of isobutyraldehyde with aqueous formaldehyde in a cascade of stirred vessels in the presence of an alcohol and of an alkali metal hydroxide as a catalyst.

6 Claims, 1 Drawing Figure

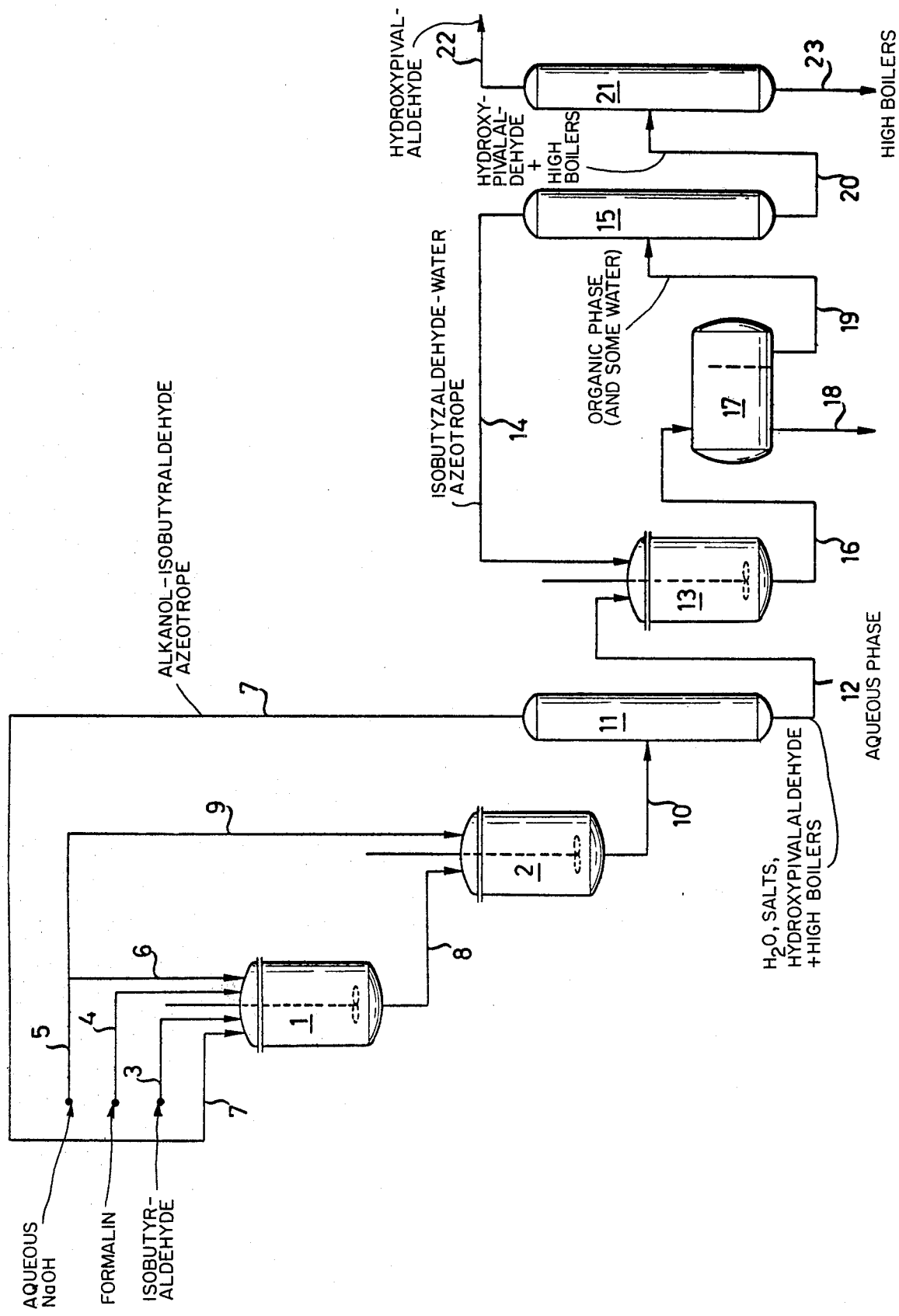

PROCESS FOR THE CONTINUOUS PREPARATION OF HYDROXYPIVALDEHYDE

The present invention relates to a process for the continuous preparation of hydroxypivalic aldehyde.

It has been proposed to prepare hydroxypivalaldehyde (hydroxypivalic aldehyde) by an aldol addition reaction of formaldehyde with isobutyric aldehyde in the presence of catalytic amounts of bases.

Although the isobutyric aldehyde is used in substantially pure form, the formaldehyde is in general used in the form of an aqueous solution of 20 to 40% strength. It has, however, also been proposed to use an alcoholic formaldehyde solution of paraformaldehyde. Aqueous solutions or suspensions of alkali metal hydroxides or alkaline-earth metal hydroxides, alkali metal carbonate solutions, amines or basic ion exchangers are used as catalysts. The reaction temperature of the known processes varies within the range from 0° to 150°C. Furthermore, in the known processes, the quantitative ratios in which the reactants are reacted are different. It has also been proposed to add a formalin solution at 65° to 70°C to a mixture consisting of isobutyric aldehyde in excess and a potassium carbonate solution and to obtain, after the reaction has been terminated, the hydroxypivalic aldehyde from the separated organic phase by distillation.

In general, a heterogeneous mixture, consisting of isobutyric aldehyde and an aqueous formalin solution, is placed in the reaction vessel and the aldol addition reaction is then carried out within a certain period by the addition of the alkaline catalyst. Because of side reactions, for example the Cannizzaro reaction, the catalyst is consumed and reacted to form the salts of the corresponding organic acids, for example, formic acid, isobutyric acid or hydroxypivalic acid.

The hydroxypivalic aldehyde obtained by the aldol addition reaction is a highly reactive compound. In the aldol addition reaction, the hydroxypivalic aldehyde is partially converted to hydroxy neopentyl hydroxypivalate by a Tischtschenko reaction.

It is very difficult to obtain hydroxypivalic aldehyde from a heterogeneous reaction mixture consisting of unreacted starting products, hydroxypivalic aldehyde, hydroxyneopentyl hydroxypivalate and other compounds having an elevated boiling point, alkali metal salts of organic acids, and water, with the least possible losses because, with the exception of the salts of the organic acids, all components of the reaction mixture are present in both phases, that is the organic phase and the aqueous phase. Thus, a technically complicated, separate working up of both phases will be necessary. The separation of the water from the reaction mixture by distillation leads to considerable losses of hydroxypivalic aldehyde as the latter is volatile with water vapor.

It has also been proposed to use and excess of 2 to 4 moles of isobutyric aldehyde per mole of formaldehyde for the aldol addition reaction, so that the amount of organic phase is considerably larger than that of the aqueous phase. Thereby the proportion of organic products in the aqueous phase is low, so that the latter can be rejected without considerable losses. This process, however, has the disadvantage that more by-products are obtained in the organic phase because of the excess isobutyric aldehyde.

Furthermore, it is known from U.S. Pat. No. 2,863,878 that the aldol addition reaction can be carried out in the presence of alcohols, for example methanol. This enables the reaction to be carried out in a homogeneous reaction mixture. As compared with other known heterogeneous processes, a smaller amount of alkali is necessary. In this process, formalin is added to a mixture of isobutyric aldehyde in excess and methanol, the formalin containing the sodium hydroxide necessary for the aldol addition reaction (4.25 grams of NaOH per mole of mixture) in a dissolved form. The reaction is carried out at 10° to 15°C. To obtain a complete reaction, a reaction time of nearly 3 hours in necessary. Because of the long reaction time, a continuous process would require large, complicated plants.

Furthermore, a process for the continuous preparation of neopentyl glycol and i-butanol has been described in U.S. Pat. No. 3,340,312. The hydroxypivalic aldehyde obtained as intermediate product is not separated, but hydrogenated, together with the isobutyric aldehyde used in a considerable excess amount (molar ratio of formaldehyde to isobutyric aldehyde 1:3), to form neopentyl glycol and i-butanol. The formaldehyde is used in the form of an aqueous solution. The concentration of the sodium hydroxide solution used as catalyst is 0.2%. At temperatures within the range of from 9° to 15°C, about 50 minutes are necessary for carrying out the aldol addition reaction.

Very good results are obtained in the aldol addition reaction by placing a mixture of isobutyric aldehyde in excess (excess amount of 10 to 20 %), formalin and methanol in a reaction vessel and then adding the aldolization catalyst in the form of a concentrated sodium hydroxide solution at temperatures within the range from 30° to 70°C, preferably 45° to 55°C. Under these conditions, the reaction is terminated after only 15 to 20 minutes. This discontinuous process has the further advantage that a considerably smaller amount of catalyst and of isobutyric aldehyde in excess is necessary.

Although the above discontinuous process is obviously superior to the known processes, it has been necessary in industry to find a continuous process for preparing and purifying hydroxypivalic aldehyde. By using a stirred vessel as reaction vessel for the continuous reaction, the extents of conversion and yields obtained by the discontinuous process could not be obtained. On the one hand, some of the reactants leave the reaction zone after a short time without having reacted, whereby the extent of conversion is reduced, while on the other hand reaction products formed stay too long in the alkali medium and are further reacted to by-products, thus causing decreased yields.

To obtain the shortest possible mean residence time in the continuous process, several reaction vessels have been connected in series, that is a cascade of stirrer vessels has been used. It appeared, however, that this measure alone was not sufficient for obtaining a preceptible improvement, that is a complete conversion and a high yield of hydroxypivalic aldehyde.

The present invention provides a process for the continuous preparation of hydroxypivalic aldehyde by a homogeneous reaction of isobutyric aldehyde with an aqueous formaldehyde solution at a temperature from 30°to 70°C. in the presence of an aliphatic alcohol having 1 – 4 carbon atoms, preferably methanol, and using an alkali solution as a catalyst. In the method, an aqueous alkali solution of 30 to 50% strength, preferably 40 – 50%, is present in the individual stirred vessels of a cascade of two or more of such vessels, in an amount from 0.5 to 4.0 grams per mol of reaction mixture. After termination of the aldol addition reaction, any unreacted isobutyraldehyde (which may be present in the reaction mixture in up to 100% excess over the stoichiometric amount) is distilled off as an azeotrope with the alcohol. The azetropic mixture is returned to the first stirred vessel. Further steps in the process include separating the distillation residue into an aqueous and an organic phase by the addition of 50 to 500 grams of isobutyraldehyde per mole of hydroxypisaldehyde produced, freeing the organic phase from water and isobutyric aldehyde by azeotropic distillation, returning the recovered isobutyric aldehyde with the water dissolved therein into the separation of the phases and obtaining pure hydroxypivalic aldehyde from the residue of the azeotropic distillation by vacuum distillation.

The process in accordance with the invention shows that the good results obtained in the discontinuous process can also be obtained in a continuous process using a cascade of two or more stirred vessels, and that even higher yields can be obtained by adding the aldolization catalyst not only to one stirred vessel, but by putting it into all stirred vessels of the cascade. This effect of the process in accordance with the invention was surprising and could not be foreseen.

In the process in accordance with the invention, not only the ratio of the catalyst distribution, but also the ratio by volume of the reaction mixture in the individual vessels of the cascade can be varied. Good results are obtained, for example, by operating a cascade consisting of two stirrer vessels in a manner such that in both vessels the volumes of reaction mixture and catalyst are almost equal. Slight variations of these ratios are not critical and have no appreciable effect on the yields.

As starting products for the process in accordance with the invention technically pure isobutyric aldehyde, an aqueous formaldehyde solution of 30 to 40% strength and a highly concentrated aqueous sodium hydroxide solution of 30 to 50% strength, preferably 40 to 50% strength, are advantageously used. By the addition of aliphatic alcohols with 1 to 4 carbon atoms, preferably methanol, in an amount of the order of, or approximately equal in weight to, as is apparent from the Example, the amount of water present, a homogeneous reaction is obtained. The amount is isobutyric aldehyde exceeding the stoichiometric amount is of 0 to 100%, preferably 10 to 20%. The catalyst amount needed of 0.5 to 4.0 grams of alkali compound per mole of reaction mixture, preferably 0.8 to 1.2 grams of alkali compound per mole of reaction mixture or about 1 % calculated on the formed hydroxypivalic aldehyde, is particularly small as compared with the known processes. Sodium hydroxide is preferably used as catalyst. The ratio of the sum of the reactants (isobutyric aldehyde and formaldehyde) to the sum of the diluents (water and methanol) is advantageously within the range of from 0.7 to 1.3, preferably about 1.0. The process in accordance with the invention is carried out at temperatures within the range of from 30° to 70°C, preferably 45°- to 55° C, the liberated heat of reaction being eliminated continuously. The aldol addition reaction is terminated after 15 to 25 minutes, so that in the process in accordance with the invention a space-time yield of hydroxypivalic aldehyde of 800 to 1,400 grams per liter of the total reaction mixture is obtained per hour. In the process in accordance with the invention higher or smaller space-time yields can be obtained, depending on the reaction temperature and the catalyst amount chosen.

Although no space-time yields have been indicated for the known processes, smaller space-time yields can be deduced from the reaction times, which are considerably longer in many cases.

The present invention provides not only a process for the continuous preparation of hydroxypivalic aldehyde under determined reaction conditions, but also the purification of hydroxypivalic aldehyde from the reaction mixture.

After the aldolization of formalin and isobutyric aldehyde has been terminated, the aliphatic alcohol added and the unreacted isobutyric aldehyde are distilled off in a fractionating column and returned to the process.

For separating the salts of the organic acids and a part of the water, a separation into an aqueous and an organic phase, called separation of the phases, is brought about by the addition of isobutyric aldehyde. The aqueous phase contains substantially the total amount of the salts of the organic acids, a part of the water and isobutyric aldehyde, and, according to their solubility, the reaction products hydroxypivalic aldehyde and hydroxypentyl hydroxypivalate. Because the volume of the aqueous phase is small as compared with that of the organic phase, the amounts of reaction products dissolved therein are insignificant; thus an additional working up is not necessary. However, if desired, these amounts may also be recovered, for example by extracting with isobutyric aldehyde and combining thhe extract with the organic phase.

The organic phase, which is now free from the salts of the organic acids and contains, in addition to hydroxypivalic aldehyde, water, isobutyric aldehyde and hydroxyneopentyl hydroxypivalate, is freed, at the same time, from water and isobutyric aldehyde by distillation under atmospheric pressure, without losses of hydroxypivalic aldehyde. This measure is, particularly advantageous as compared with known processes, because the water is eliminated in the form of an azeotropic mixture with isobutyric aldehyde boiling at 59.5°C before the distillation of the hydroxypivalic aldehyde which is volatile with water vapor.

This mixture is returned to the separation of the phases after the separation of the water, which partially separates at about 20°C on condensation. Slight losses of isobutyric aldehyde caused by removing the aqueous phase after the separation of the phases must be replaced if the isobutyric aldehyde dissolved therein is not recovered by the azeotropic distillation.

The problem of separating the water and the salts of the organic acids, a prerequisite to an economic preparation of pure hydroxypivalic aldehyde from the crude reaction mixture of the aldol addition reaction, is solved by using a cycle of isobutyric aldehyde in accordance with the invention. In the process in accordance with the invention amounts of 50 to 500 grams, preferably 100 to 200 grams, per mole of reaction mixture of isobutyric aldehyde are used; these amounts are sufficient for eliminating the water which has remained in the organic phase, as an azeotrope on distillation. Another advantage is that by this measure a hydroxypivalic aldehyde of very high percentage, that is of about 90% strength, is obtained in the sump of the azeotropic distillation column. To obtain pure hydroxypivalic aldehyde a vacuum distillation may follow.

Hydroxypivalic aldehyde has a wide range of application. It serves, for example, as starting product for synthetic resins or for the preparation of hydroxypivalic acid or neopentyl glycol.

The process of this invention is illustrated diagrammatically by way of example in the accompanying flow chart. For simplifying, the coolers, heaters, heat exchangers and pumps are not shown in the flow chart.

As reactor, a cascade is used consisting of the two stirred vessels 1 and 2. Stirred vessel 1 is continuously charged with 196 moles of isobutyric aldehyde via line 3, with 200 moles of an aqueous formalin solution of 37% strength via line 4, with 2.5 moles of an aqueous sodium hydroxide solution of 50 % strength via lines 5 and 6, with 344 moles (11 kilograms) of methanol via line 7 and with isobutyric aldehyde in excess (35 moles). The reaction temperature in stirred vessel 1 is about 50°C. The reaction mixture is conducted into stirred vessel 2 via line 8, this stirred vessel 2 being charged via line 9 with 2.5 moles of an aqueous sodium hydroxide solution of 50% strength. In stirred vessel 2 the aldol addition reaction is terminated at about 50°C. The homogeneous mixture flows from stirred vessel 2 via line 10 into distillation column 11. As head product of distillation column 11 azeotrope, boiling at 57.3°C, consisting of unreacted isobutyric aldehyde and methanol, is returned to stirred vessel 1 via line 7. The sump product of distillation column 11 is conducted via line 12 to stirred vessel 13, which is additionally charged via line 14 with the head product of distillation column 15, consisting of the azeotrope of isobutyric aldehyde and water boiling at 59.5°C. The reaction mixture in stirred vessel 13 flows via line 16 into separator 17, where separation into an aqueous and an organic phase is carried out. The aqueous phase is removed from separator 17 via line 18; the organic phase in separator 17 is introduced via line 19 into distillation column 15. While the head product of distillation column 15 is conducted via line 14 into stirred vessel 13, the sump product of distillation column 15 is introduced into vacuum distillation aparatus 21 via line 20. As head product of the vacuum distillation column, pure hydroxypivalic aldehyde is distilled off via line 22 at 88° to 90°C under a pressure of 15 millimeters of mercury while the distillation residue of about 2 kilograms, containing hydroxyneopentyl hydroxypivalate and other high-boiling reaction by-products, is withdrawn via line 23.

The following Example serves to illustrate the invention, but is not intended to limit it.

EXAMPLE 14.7 kilograms of isobutyric aldehyde of 96% strength (196 moles), 16.2 kilograms of an aqueous formalin solution of 37% strength (200 moles) and 0.2 kilograms of an aqueous sodium hydroxide solution of 50% strength (2.5 moles) were introduced, per hour, into stirred vessel 1 of the a cascade like that shown in the accompanying FIG. Furthermore, 2.5 kilograms per hour of isobutyric aldehyde (35 moles) and 11.0 kilograms per hour of methanol were conducted from column 11 to stirred vessel 1. After a medium residence time of about 10 minutes, the mixture flowed into stirred vessel 2 of the cascade, which was furthermore charged with 0.2 kilogram per hour of an aqueous sodium hydroxide solution of 50% strength. The medium residence time in stirred vessel 2 was also adjusted to about 10 minutes. In stirred vessels 1 and 2 the heat of reaction was eliminated by indirect cooling and the reaction temperature maintained at about 50°C.

In distillation column 11, an azeotrope boiling at 57.3°C and consisting of isobutyric aldehyde in excess and methanol was completely distilled off and returned via line 7 to stirred vessel 1. The sump product of distillation column 11 was pumped via line 12 into stirred vessel 13, where 30 kilograms of the azeotrope of isobutyric aldehyde and water boiling at 59.5°C and which had been returned as head product of distillation column 15 via line 14, were added. The mixture in stirred vessel 13 was withdrawn at the bottom via line 16 and separated in separator 17 into an aqueous and an organic phase.

The aqueous phase of separator 17 was discharged via line 18. The organic phase was pumped via line 19 into distillation column 15 and freed from isobutyric aldehyde and water by azeotropic distillation; the sump product of distillation column 15 was pumped via line 20 into the vacuum-distillation column 21; the reaction mixture was distilled in vacuo in distillation column 21, for example with the aid of a thin layer evaporator; the hydroxypivalic aldehyde withdrawn as head product via line 22 boiled at 88°to 90°C under a pressure of 15 millimeters of mercury. 18.0 kilograms per hour of a hydroxypivalic aldehyde of 99% strength having a melting point of 92°C were obtained, corresponding to a yield of 87% of the theoretical. The distillation residue of about 2 kilograms per hour contained hydroxyneopentyl hydroxypivalate in addition to other reaction by-products of higher boiling point.

What is claimed is:
1. A process for the continuous preparation and recovery of hydroxypivalaldehyde which comprises:
   (1) reacting isobutyraldehyde and formaldehyde in a homogeneous reaction mixture at a temperature from 30°C. to 70°C. in a first stirred vessel, said said reaction mixture being formed by introducing into said vessel an aqueous formaldehyde solution, isobutyraldehyde in a stoichiometric amount or in excess up to 100 percent, an aqueous 30 percent to 50 percent sodium hydroxide solution as a catalyst, said sodium hydroxide being present in an amount of 0.5 to 4.0 grams per mol of hydroxypivalic aldehyde produced, and an alkanol having 1 to 4 carbon atoms, said alkanol being present in an amount approximately equal in weight to the amount of water contributed by said aqueous formaldehyde solution and said aqueous sodium hydroxide solution, the ratio of the sum of the isobutyraldehyde and formaldehyde reagent to the sum of the water and alkanol being from 0.7 to 1.3;
2. introducing the reaction mixture from said first stirred vessel into at least one additional stirred vessel for further reaction at a temperature from 30°to 70°C., said additional stirred vessel being connected with said first stirred vessel in a cascade arrangement, and adding additional catalyst solution to said additional stirred vessel in the same amount as is present in said first stirred vessel;
3. distilling unreacted isobutyraldehyde from the reaction mixture, after reaction in said additional stirred vessel, as an azeotrope with said alkanol and returning the distillate to said first stirred vessel;
4. separating the undistilled residue into an aqueous phase and an organic phase in a separation zone by the addition thereto of 50 to 500 grams of isobutyr- aldehyde per mol of hydroxypivalaldehyde formed in the reaction;
5. distilling the organic phase to remove water and isobutyraldehyde as an azeotrope thereof and returning the isobutyraldehyde, with dissolved water therein, to the separation zone; and
6. vacuum distilling the undistilled residue to obtain pure hydroxypivalaldehyde.

2. A process as in claim 1 wherein said aqueous sodium hydroxide solution has a concentration from 40 – 50%.

3. A process as in claim 1 wherein said alkanol is methanol.

4. A process as in claim 1 wherein said isobutyraldehyde is present in an excess of 10 – 20% of the stoichiometric amount.

5. A process as in claim 1 wherein said reaction is carried out at a temperature from 45° to 55°C.

6. A process as in claim 3 wherein the ratio of the sum of the isobutyraldehyde and formaldehyde reagents to the sum of the water and methanol diluents is about 1.

* * * * *